(12) United States Patent
Noyes

(10) Patent No.: US 8,551,402 B1
(45) Date of Patent: Oct. 8, 2013

(54) MOBILE ASSAY FACILITY AND METHOD OF USING SAME TO PROCURE AND ASSAY PRECIOUS METALS

(76) Inventor: Chris M. Noyes, Virginia Beach, VA (US)

( * ) Notice: Subject to any disclaimer, the term of this patent is extended or adjusted under 35 U.S.C. 154(b) by 127 days.

(21) Appl. No.: 13/364,422

(22) Filed: Feb. 2, 2012

Related U.S. Application Data

(63) Continuation-in-part of application No. 13/136,811, filed on Aug. 11, 2011.

(51) Int. Cl.
*G01N 21/00* (2006.01)
(52) U.S. Cl.
USPC .................. 422/63; 422/64; 422/65; 422/50; 422/500; 422/501; 422/502; 422/503; 436/180; 296/24.3
(58) Field of Classification Search
USPC ............... 422/63–65, 50, 500–503; 436/180; 296/24.3
See application file for complete search history.

(56) References Cited

U.S. PATENT DOCUMENTS 4,462,879 A * 7/1984 Castellanos et al. .......... 205/723
2012/0030097 A1* 2/2012 Hagan et al. .................... 705/39

* cited by examiner

*Primary Examiner* — Jyoti Nagpaul
(74) *Attorney, Agent, or Firm* — David L. Banner

(57) ABSTRACT

A self-contained, mobile assay facility built in a modified armored truck is completely equipped to melt and assay precious metals, particularly gold and silver. An induction furnace melts the metal that is then poured into an ingot. The ingot is weighed and analyzed using an XRF alloy analyzer and the percentage of gold and/or other metals recorded. The value of the gold at current market prices is calculated and the assay and the value of the ingot is printed and given to the seller. The seller may opt to receive the ingot and pay the assayer an assay fee. Alternately, the seller may ask to be paid cash, by bullion, wire transfer, or by an open hedge. Either a transfer or hedge is initiated and confirmed from the assay facility. The ingots may be safely stored or shipped directly from the mobile facility to a wholesaler for further processing.

20 Claims, 15 Drawing Sheets

MOBILE ASSAY FACILITY AND METHOD OF USING SAME TO PROCURE AND ASSAY PRECIOUS METALS

RELATED APPLICATIONS

This application is a Continuation-in-Part application of U.S. patent application Ser. No. 13/136,811 filed Aug. 11, 2011 titled Mobile Assay Facility and Method of Using Same to Procure and Assay Precious Metals which is included herein in its entirety by reference.

FIELD OF THE INVENTION

The invention pertains to facilities for assaying precious metals and, more particularly, to a secure, mobile, self-contained assay facility and a method of using the facility to procure, assay, and process gold and other precious metals.

BACKGROUND OF THE INVENTION

The increasing demand for gold and other precious metals for industrial processes, investments, and other uses has caused the market prices for such metals to increase to record levels. The high market price of gold has prompted owners of unused, unwanted jewelry to sell that jewelry through brokers such as pawn shops, jewelry stores, and other establishments equipped to purchase such used jewelry from the public. As used herein, the term pawn shop will be used to refer to any and all such receivers of precious metals. Further, for simplicity, the term gold will be assumed to include other precious metals such as, but not limited to, silver, platinum, copper, etc.

After the pawn shop has purchased gold, most likely as assorted jewelry from several individual sellers, the pawn shop must either melt the purchased gold or sell the gold as-is to a processor of precious metals.

SUMMARY OF THE INVENTION

In accordance with the present invention there is provided a mobile assay facility and a method of using the mobile assay facility. A vehicle, ideally an armored truck modified to raise the ceiling height in the cargo area to allow an adult human to stand upright therein, is completely equipped to melt and assay precious metals, particularly gold and gold alloys.

An induction furnace designed to melt precious metals is installed in the vehicle. A three-phase, diesel powered electrical generator, typically placed on the vehicle's roof and fueled from the vehicle's fuel supply, is used to provide electrical power to the induction furnace as well as other electrically powered apparatus used in the assaying process. Optionally, the vehicle (typically with the exception of the induction furnace) may be powered from an external power source.

An apparatus to provide cooling water to the induction furnace and a quench tank for cooling ingots are also located in the vehicle.

An accurate scale, typically an analytical balance is used to weigh precious metals, and an X-ray fluorescence (XRF) alloy analyzer is used to provide an accurate assay of the content of an ingot.

In operation, a seller of scrap precious metal, typically unwanted or broken jewelry, brings the unwanted precious metal to the mobile assay facility where it is melted and poured into an ingot. After the ingot is cooled and dried, it is weighed and the exact weight is recorded in a computer. The ingot is then analyzed with the XRF analyzer and this accurate assay of the ingot is then recorded in the computer.

A communications apparatus within the mobile assay facility is used to determine the current price of the precious metal of interest (usually gold) and that price is also entered into the computer. Using the data now in the computer, the value of the specific precious metal in the ingot is calculated.

The seller has several options. He or she may wish to receive the melted ingot. In this case the seller pays the assayer a fee for the melting and assay and then leaves with the ingot.

If the seller wishes to receive cash for the ingot, a cash dispenser in the mobile assay facility is used to pay the seller the amount due.

If the seller wishes to receive payment for the ingot as a wire transfer to his or her account, a wire transfer is initiated from within the mobile assay facility. Once a confirmation number is received from the issuing bank, the seller leaves the facility. The seller may be given an opportunity to communicate with his or her own bank to provide them the confirmation number.

It will be recognized that other payment arrangements may be made with the seller. For example, the surrendered precious metals may be processed and assayed so that the seller understands exactly how many ounces of metal that he/she has. The processor (e.g., Assay on Wheels) then takes possession of the metal but does not immediately pay the seller. Rather, the seller then has the option to call the buyer/processor when the price of the surrendered metal reaches a certain price that's acceptable to the seller. The buyer/processor then hedges the metal into the market and pays the seller at that future time.

If purchased from the seller, the ingot may be placed in a safe within the vehicle or, alternately, one or more ingots may be shipped to a processor of precious metals. First, the ingot (s) are placed in a secure case (e.g., a turtle box), have one or more security seals affixed, have the turtle box placed in a standard FedEx or other carrier's shipping container that may then be dropped at any FedEx or other appropriate carrier's office or at any appropriate pickup box.

It is, therefore, an object of the invention to provide a mobile, self-contained assay facility completely equipped to melt and assay scrap precious metal.

It is a further object of the invention to provide a mobile, self-contained assay facility that is constructed in a modified armored truck.

It is another object of the invention to provide a mobile, self-contained assay facility where scrap precious metal may be melted using an induction furnace powered by a generator forming part of the mobile, self-contained assay facility and the melted metal may be formed into ingots.

It is an additional object of the invention to provide a mobile, self-contained assay facility where ingots may be accurately assayed and wherein the current market price of gold or another precious metal may be determined so that a value may be affixed to the ingot.

It is a further object of the invention to provide a mobile, self-contained assay facility where a computer calculates the worth of the seller's scrap precious metal now in ingot form and where the seller may be paid for the precious metal in cash carried in a cash dispenser or, alternately, by a wire transfer initiated and confirmed from the mobile, self-contained assay facility.

It is a still further object of the invention to provide a mobile, self-contained assay facility security, surveillance, and communications system whereby the location, security, and other information concerning the mobile, self-contained assay facility is available at a location remote thereto.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein:

FIG. 4b is a pictorial, schematic view of the vehicle roof of FIG. 4a;

DETAILED DESCRIPTION OF THE PREFERRED EMBODIMENT

The present invention provides a mobile assay facility and a method of using the mobile facility.

Figure 1A:
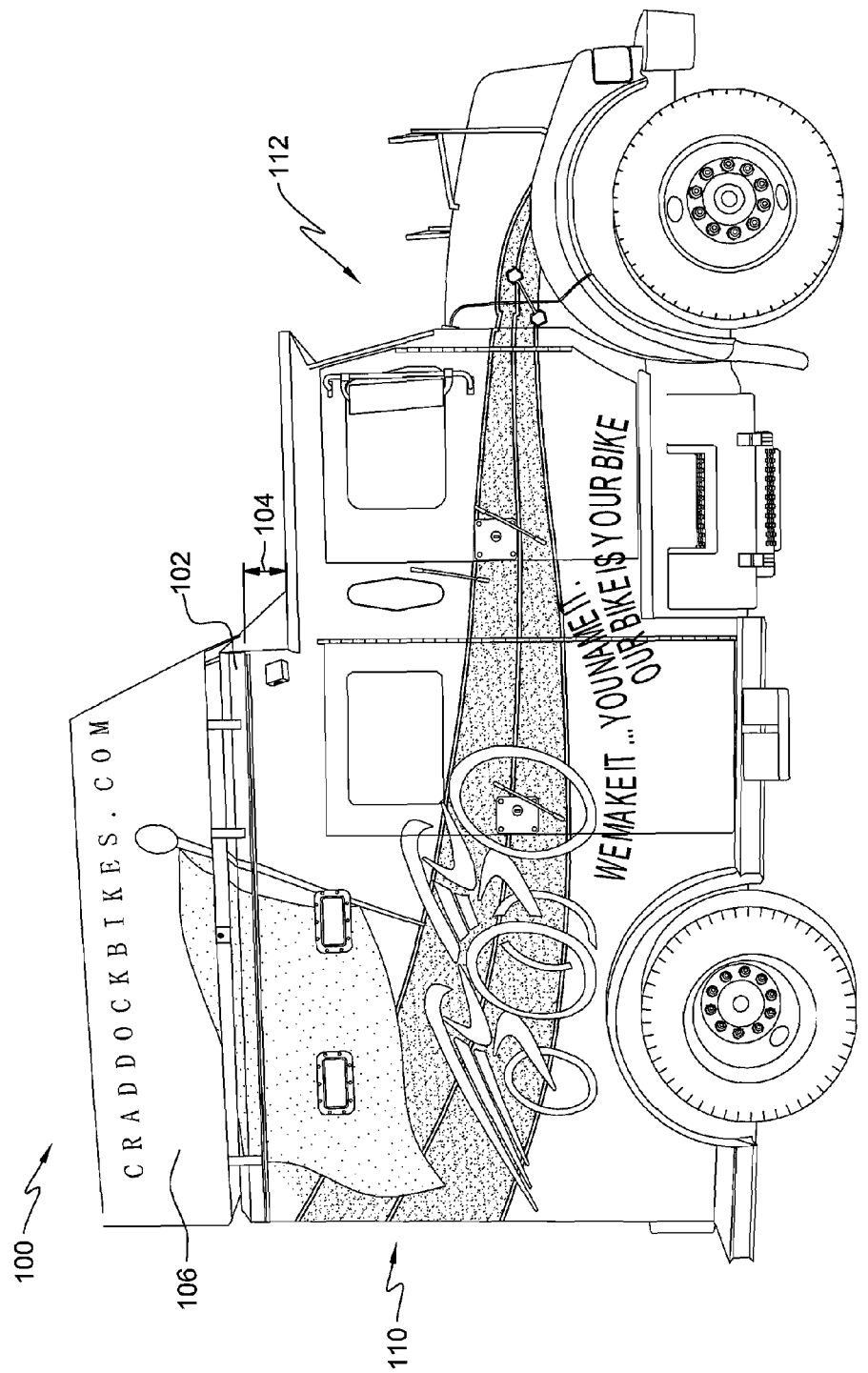
FIGS. 1a and 1b are shown right side and rear elevational pictorial, views of a vehicle adapted for use as a mobile assay facility.
Figure 1B:
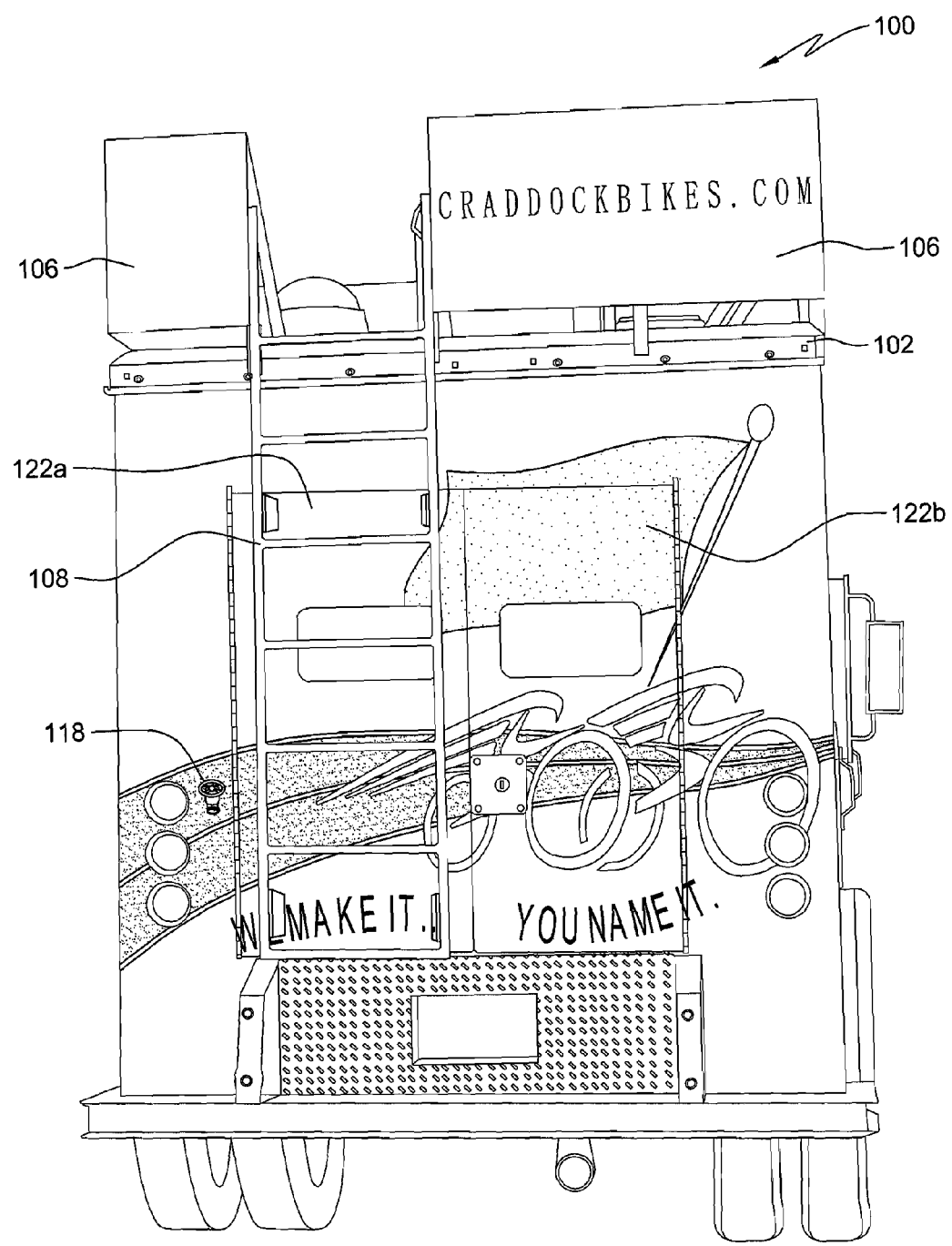

Referring first to FIGS. 1a and 1b, there are shown right side and rear elevational pictorial, drawings of a vehicle adapted for use as a mobile assay facility, generally at reference number 100. In the embodiment chosen for purposes of disclosure, a modified armored truck has been chosen to house the mobile assay facility of the invention. It will be recognized that other types of vehicles may be used to meet a particular operating circumstance or environment. Consequently, the invention is not considered limited to the armored truck chosen for purposes of disclosure. Rather, the invention is intended to include any suitable vehicle.

Vehicle 100 has been modified in that the roof 102 has been raised from its original position to allow additional inside headroom. In the embodiment chosen for purposes of disclosure, the roof has been raised approximately 18 inches as indicated by reference number 104. However, it will be recognized that height increases 104 other than 18 inches are possible and may be desirable for some applications.

The roof 102 of vehicle 100 has been strengthened, typically using polymeric foam, not shown, between the inner and outer roof layers. Approximately 16 inches of the 18 inch roof raise appears in the truck interior. The remaining approximately 2 inches of roof raise is used for roof reinforcement including the polymeric foam. In addition to strengthening the roof, the polymeric foam provides sound deadening to isolate the truck interior from noise produced by roof mounted equipment, discussed in detail hereinbelow, as well as other externally generated noise. Those of skill in the art will recognize that the roof may be strengthened in many ways and any other suitable roof-strengthening materials and or techniques may be substituted for the polymeric foam used for purposes of disclosure.

Roof skirting 106 has been added around at least a portion of the perimeter, not specifically identified of roof 102.

A ladder 108 disposed on a rear side of vehicle 100 facilitates access to roof 102. Ladder 108 is typically attached to door 122a so as to pivot out of the way when door 122a is opened. As is discussed in detail hereinbelow, roof 102 is used to support mechanical equipment necessary to support the mobile assay operation.

Figure 2A:
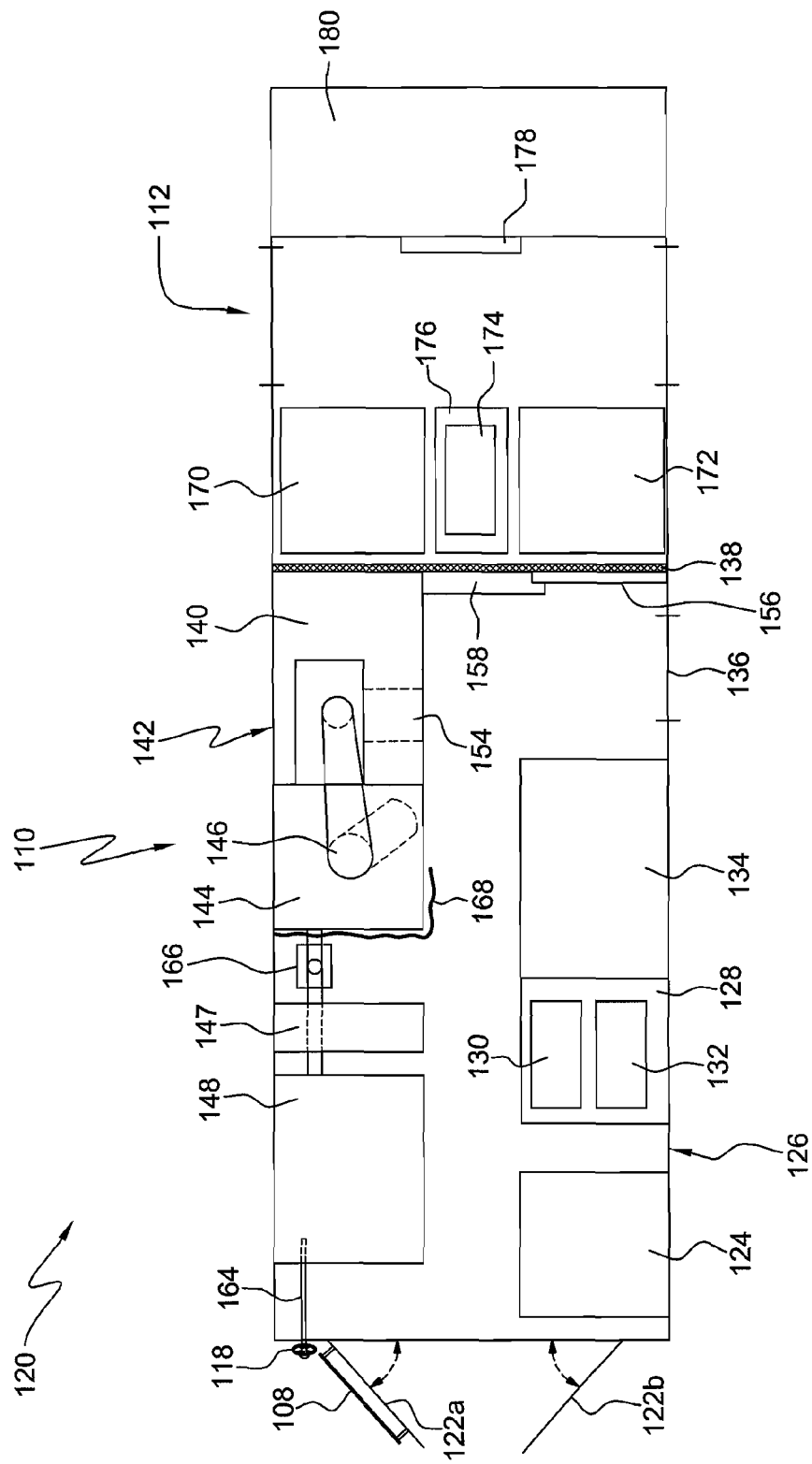
FIG. 2a is a top plan schematic view of the interior of the vehicle of FIGS. 1a and 1b.
Figure 2B:
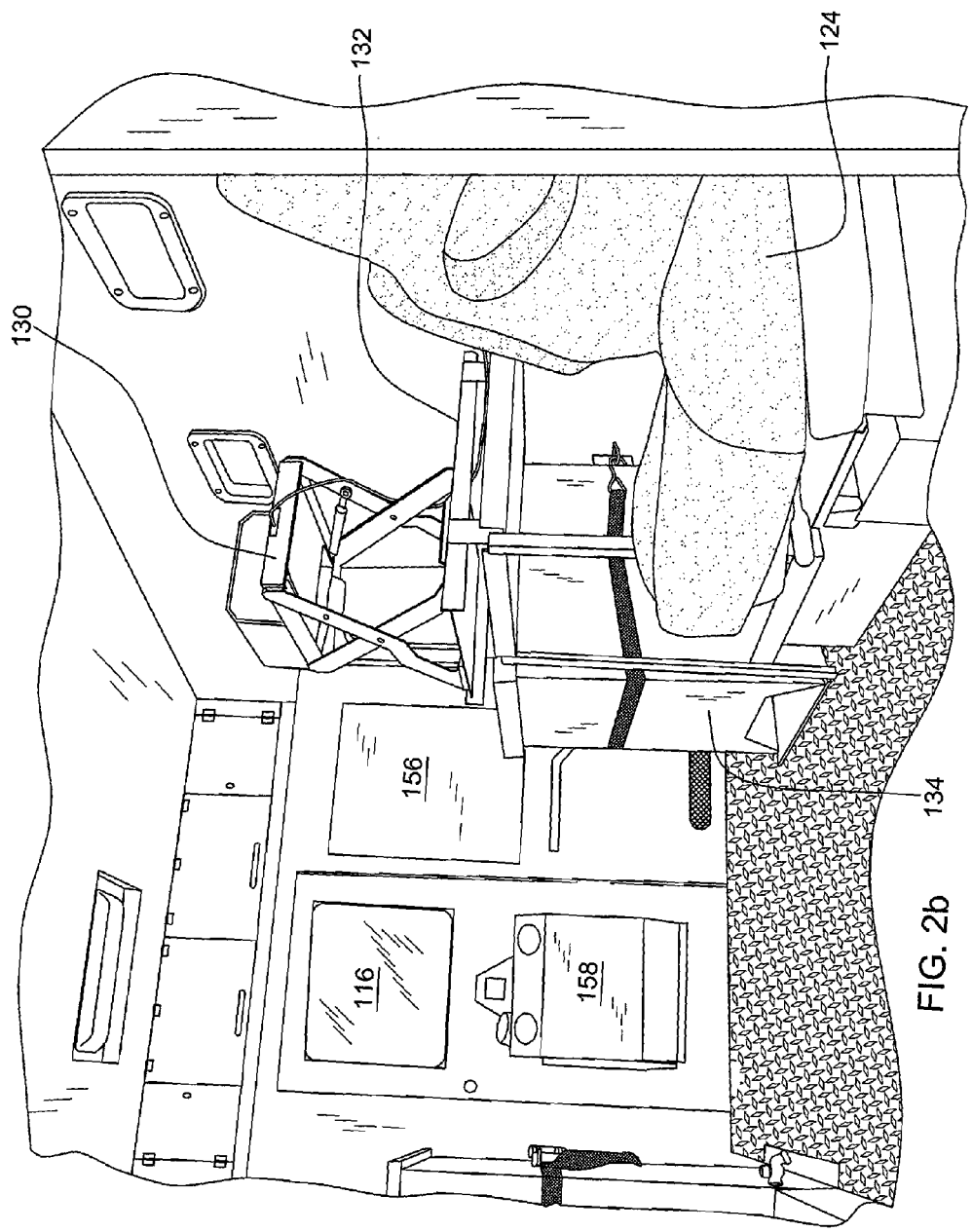
FIGS. 2b and 2c are rear elevational, pictorial, schematic views of the right and left sides, respectively, of the interior of a portion of the vehicle of FIG. 2a, FIGS. 2d, 2e, and 2f are detailed views of portions of the left side of the interior portion of the vehicle as shown in FIG. 2c.

A cooling water inlet port 118 is disposed on the rear of truck 100. Water inlet port 118 is typically a standard hose bib or spigot allowing connection of a "garden hose" to water inlet port 118 to fill induction furnace cooling tank 148 (FIG. 2a) readily from outside truck 100.

Figure 2C:
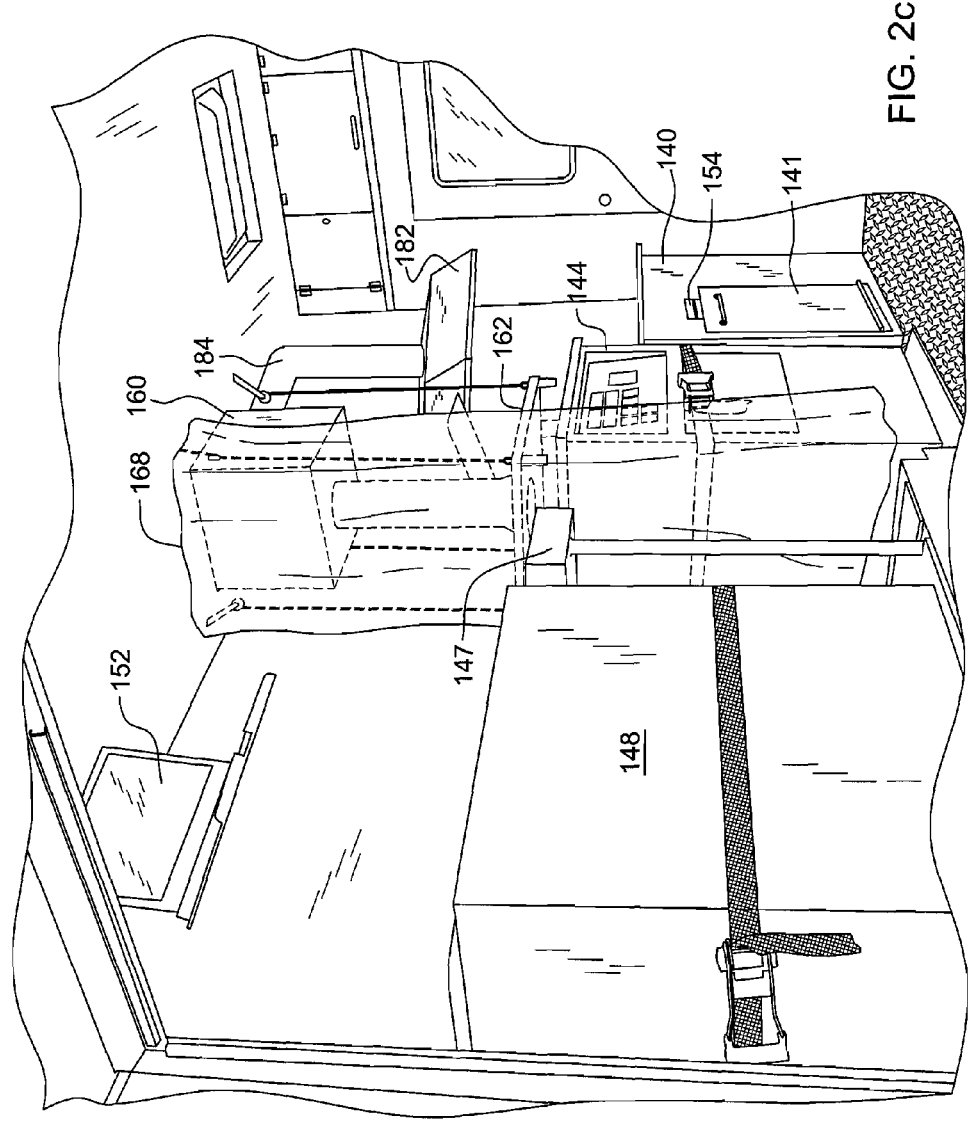

Referring now also to FIGS. 2a, 2b, 2c, 2d, 2e, and 2f there are shown a top plan schematic view (generally at reference number 120), a rear elevational schematic, pictorial view of the right interior, a rear elevational schematic, pictorial of the left interior of vehicle 100, and three detailed views of portions of the left interior shown in FIG. 2c, respectively. Floor plan 120 is, therefore, a simplified floor plan of both assay facility 110 and cab 112 of truck 100.

As is typical in armored trucks, a secure cargo compartment 110 and a cab portion 112 are separated from one another by a secure partition 138. A bullet proof window 116 allows visual communication between compartment 110 and cab 112. Electronic communication, also discussed in detail hereinbelow, is provided between compartment 110 and cab 112.

A pair of outward opening rear doors 122a, 122b form an entrance/exit to or from the interior of cargo space 110, hereinafter referred to as assay facility 110. It will be recognized that some trucks will have only a single rear door, not specifically identified.

A rear bucket seat 124 is placed adjacent rear door 122b with its back against right compartment wall 126. Seat 124 is a padded seat designed for occupant comfort and is fully equipped with a seat belt system to ensure occupant safety while vehicle 100 is in motion.

Adjacent seat 124 is work table 128 having an X-ray fluorescence (XRF) alloy analyzer 130 disposed on an upper surface thereof. A Thermo Scientific Niton® Model XL3t XRF analyzer manufactured by Thermo Fisher Scientific of Billerica, Mass. has been found suitable for the application. Typically the Thermo Scientific Niton® Model XL3t analyzer 130 is mounted on a stand, not specifically identified, to facilitate use thereof. It will be recognized that other suitable XRF analyzers and/or similar analyzers using different analysis technologies may be substituted for the Thermo Scientific Niton® Model XL3t analyzer 130 chosen for purposes of disclosure. Consequently, the invention is not considered limited to a particular analysis device or technology as any suitable analysis apparatus may be utilized.

Also located on an upper surface of work table 128 is an accurate scale, typically an Analytical Balance 132. An Ohaus Explorer® Pro analytical balance, Model EP6101N manufactured by Ohaus Corporation of Parsippany, N.J. has been found suitable for the application. As with other equipment used within assay facility 110, it will be recognized that other suitable scales or balances may be substituted for the Ohaus Model EP6101N and the invention is intended to include any suitable scale or balance.

A quench tank 134 is located between work table 128 and a side door 136.

Side door 136 is typically used as the client (i.e., seller of precious metals) entrance.

Adjacent and perpendicular to side door 136 is a secure partition 138 between the assay facility 110 and cab 112.

A safe 140 is disposed on the floor and against left wall 142 of vehicle 100 across from side door 136. Safe 140 has a flat top surface, not specifically identified, that functions as a work surface as described in more detail hereinbelow.

A second exhaust hood 182 is disposed over the work surface formed by safe 140. Second exhaust hood 182 is connected to exhaust system 160 by round duct 184.

Figure 2D:
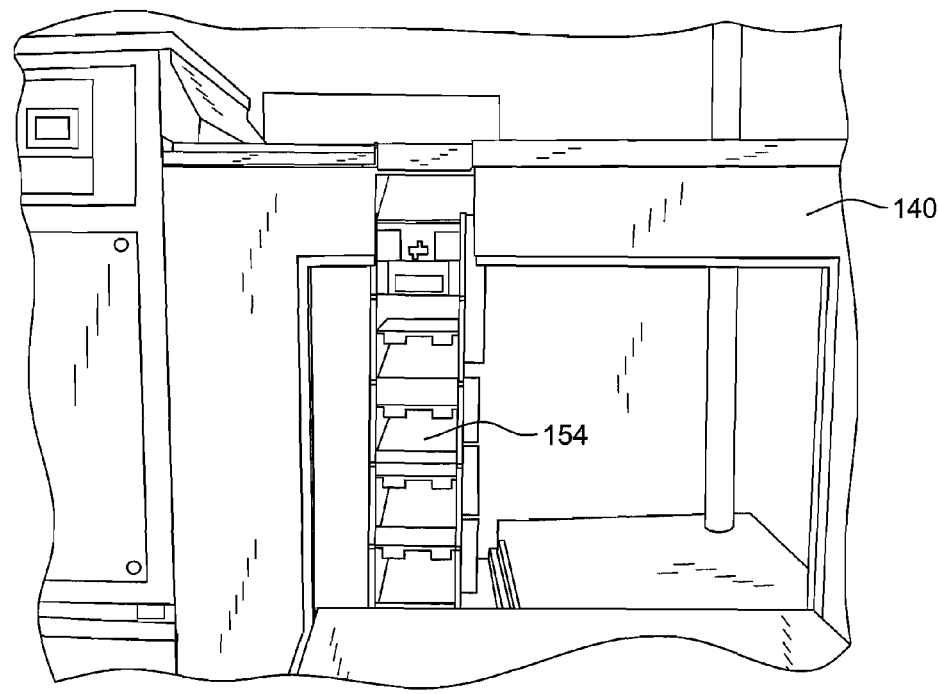
Figure 2E:
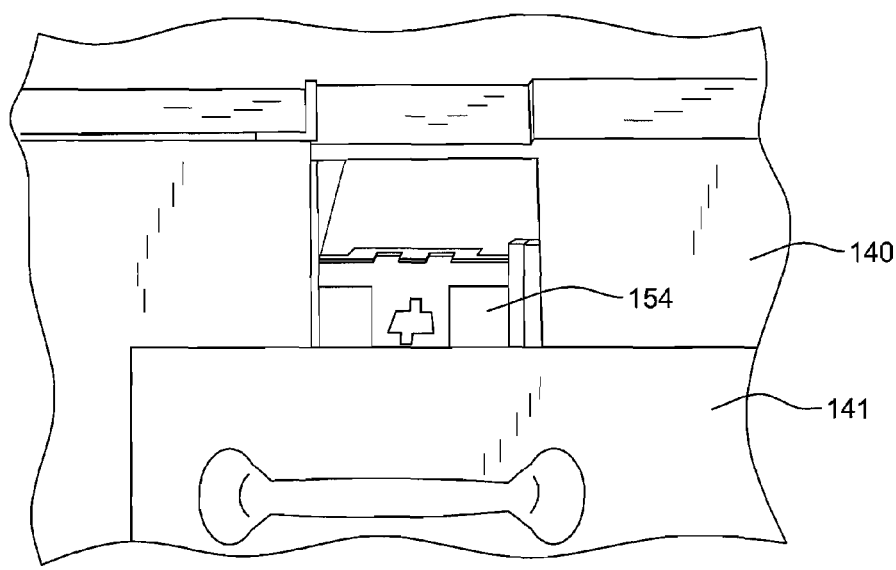

As may be seen in FIGS. 2d and 2e, a cash dispensing machine 154 is disposed within safe 140. A modification to safe 140 allows the cash dispensing outlet, not specifically identified, of cash dispensing machine 154 to be accessed from outside safe 140 through safe door 141 so that cash, not shown, may be dispensed without need to open safe 140.

Adjacent safe 140 is an induction furnace 144 having an opening 146 in an upper surface to accept a crucible. A CEIA Model F5-D/1200 manufactured by CEIA SpA of Arezzo, Italy has been found suitable for the application. It will be recognized that other similar induction furnaces may be known to those of skill in the art, any suitable one of which may be substituted for the CEIA furnace chosen for purposes of disclosure.

It will be recognized that a small arc casting furnace may be substituted for the induction furnace. Such furnaces are believed to be known to those of skill in the art and, consequently, the invention is not limited to the use of induction furnace 144 used for purposes of disclosure. Rather, any suitable melting apparatus (e.g., an arc casting furnace) may be substituted therefor.

A welding curtain 168 having magnets, not specifically identified, along an upper edge thereof may be used to enclose induction furnace 144 during operation thereby protecting a person seated in rear bucket seat 124 during a metal melting operation. Welding curtain 168 is typically a transparent curtain that allows a person seated in rear bucket seat 124 or elsewhere in the rear portion of assaying space 112 to observe the metal melting operation. The use of magnets or a track to suspend welding curtain 168 from the ceiling, not specifically identified, of truck 100 allows rapid deployment and removal of welding curtain 168.

An exhaust system, shown schematically at reference number 160, best seen in FIG. 2c, is movable along a vertical axis such that exhaust hood 162 is movable between an operational position close to crucible opening 146 and a raised, non-operational position, not shown, that allows access to a crucible, not specifically identified, disposed in crucible opening 146. Fumes collected by exhaust hood 152 are exhausted above the roof of vehicle 100 by exhaust system 160, discussed in more detail hereinbelow. Because of the nature of fumes generated in the melting of precious metals, exhaust system 160 is adapted to change the entire volume of air within assay facility 110 several times per minute. In the embodiment chosen for purposes of disclosure, exhaust system 160 changes the air in assay facility 110 approximately four times per minute. It will be recognized that exhaust system 160 may readily be modified to provide fewer or more changes of air per minute as required.

Adjacent induction furnace 144 is another work shelf 147 and then adjacent work shelf 147 is an induction furnace coolant tank 148 includes a water chiller, not specifically identified. A Dimplex Thermal Solutions Chiller; Model# JH1000-21-V has been found suitable for the application. Induction furnace cooling water tank 148 may have its interior surface, not specifically identified, coated with a ceramic or other suitable material to minimize corrosion.

Figure 2F:
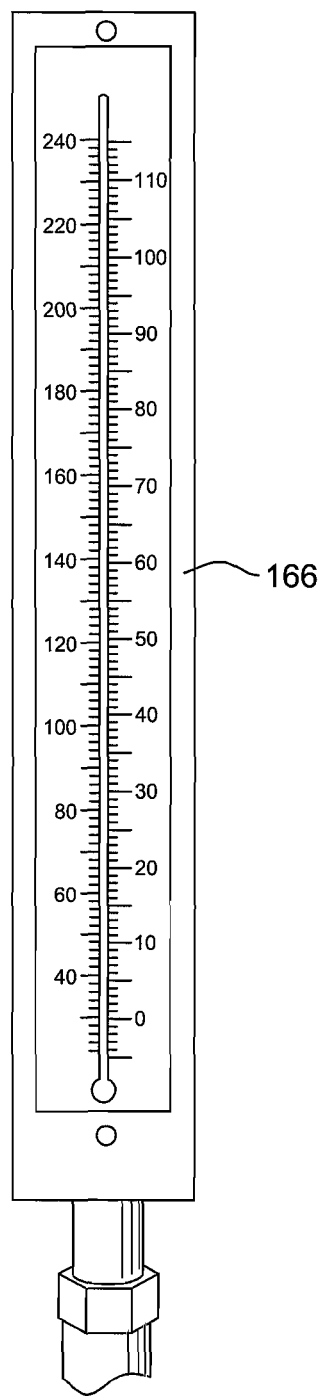

An external cooling water intake 118 disposed on the outside of truck 100 proximate door 122a is connected to cooling water line 164 that conveys water to induction furnace cooling tank 148 and the Dimplex water chiller connected thereto. Plumbing, not specifically identified, includes pipes, valves, etc. to create an adequate flow of cool water through induction furnace 144. A thermometer 166, best seen in FIG. 2f, is disposed in the plumbing to monitor the temperature of cooling water entering induction furnace 144.

A provision is included in the aforementioned plumbing to introduce compressed air to purge all lines when necessary so that damage due to freezing is eliminated.

Induction furnace cooling water tank 148 may be drained to the outside of the truck when required, the water typically being discharged adjacent a rear wheel, not specifically identified, in the rear left wheel well, not specifically identified, of truck 100.

A remote monitor 152, best seen in FIG. 2c is mounted above induction furnace coolant tank 148 and oriented such that its screen is readily visible to an occupant, not shown, of rear bucket seat 124. Remote monitor 152 is typically operatively connected to notebook computer 174, best seen in FIG. 3, located in cab are 112 of truck 100. Both notebook computer 174 and the function of remote monitor 152 are described in more detail hereinbelow.

In alternate embodiments, remote monitor 152 may be replaced by a separate notebook computer, not shown operatively connected to notebook computer 174 located in cab 112 of vehicle 100.

A fold-down work table 156 is stored flat against partition 138. When needed, fold-down work table may be raised and supported by a leg, not specifically identified that may be stored adjacent work shelf 147.

An air conditioning/Heat unit 158 is also mounted against partition 138. Air conditioning unit 158 serves to cool assay space 110 of truck 100.

Figure 3:
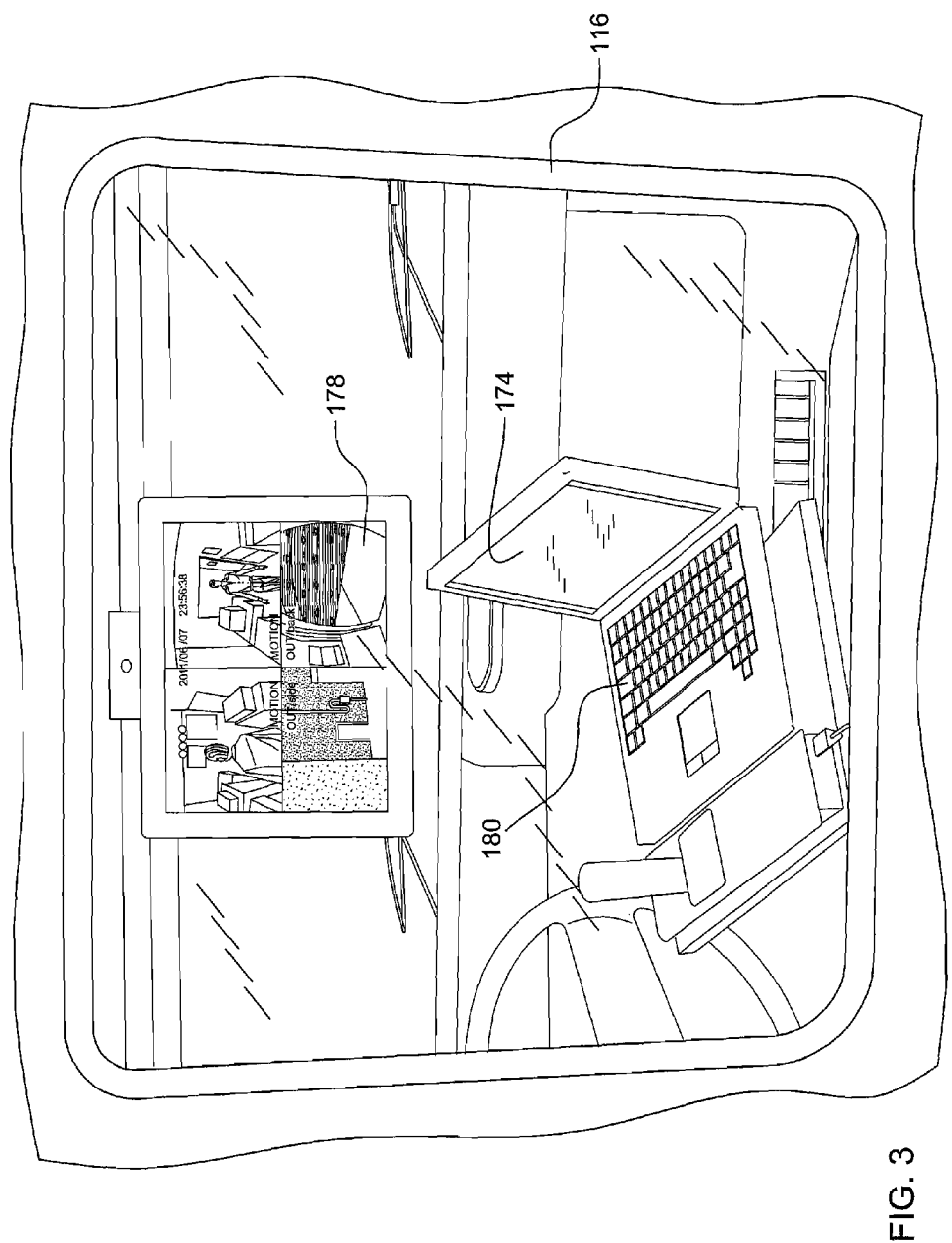
FIG. 3 is a pictorial, schematic view of a cab portion of the vehicle of FIGS. 1a, 1b, and 2a as viewed from a rear portion of the vehicle.

Referring now also to FIG. 3, there is shown a pictorial view of cab 112 as viewed through window 116 from assay facility 110.

The cab portion 112 of vehicle 100 has a driver's air seat 170 in a position normally occupied by a driver's seat. A second, passenger's air seat 172 is disposed at the right side of cab 112.

Between driver's air seat 170 and passenger's air seat 172 is a notebook computer 174 supported on a custom support stand 176. Support stand 176 swivels between a stored position and an in-use position. When in its stored position, support stand 176 allows unencumbered driving of vehicle 100. When needed, support stand 176 may swivel selectively to either a driver's position or a passenger's position allowing ready access to notebook computer 174 by either a driver or a passenger.

A variety of security communication system components 180 are mounted, in, on, or above the dashboard of vehicle 100. These security and communication system components, not individually identified in FIG. 2, are discussed in detail hereinbelow.

A security video monitor 178 is typically mounted above the windshield, not specifically identified, of vehicle 100.

Security monitor 178 is mounted to be readily visible to either a driver or a passenger within cab 112 of vehicle 100.

Figure 4A:
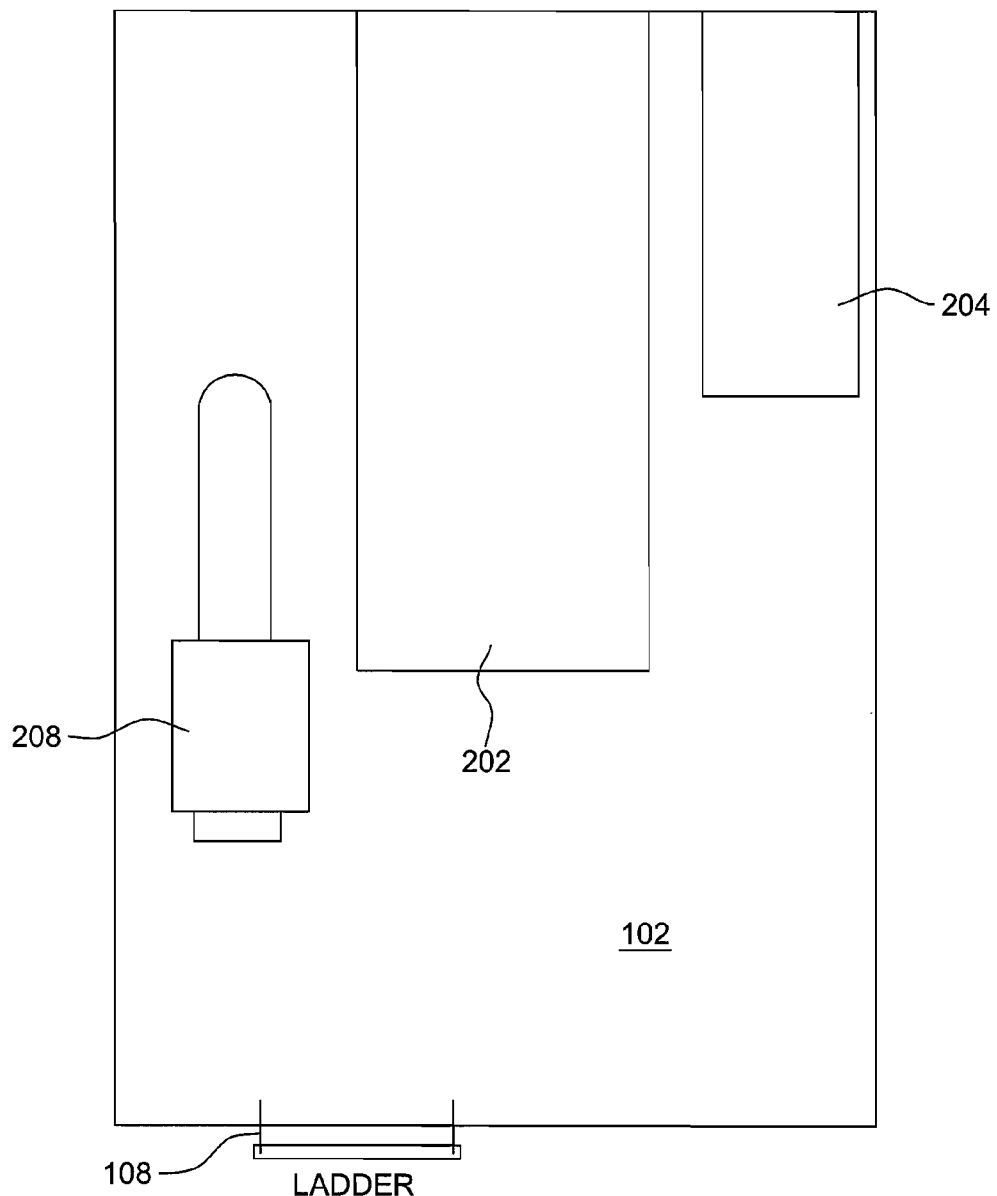
FIG. 4a is a top plan schematic of the roof of the vehicle of FIGS. 1a and 1b.
Figure 4B:
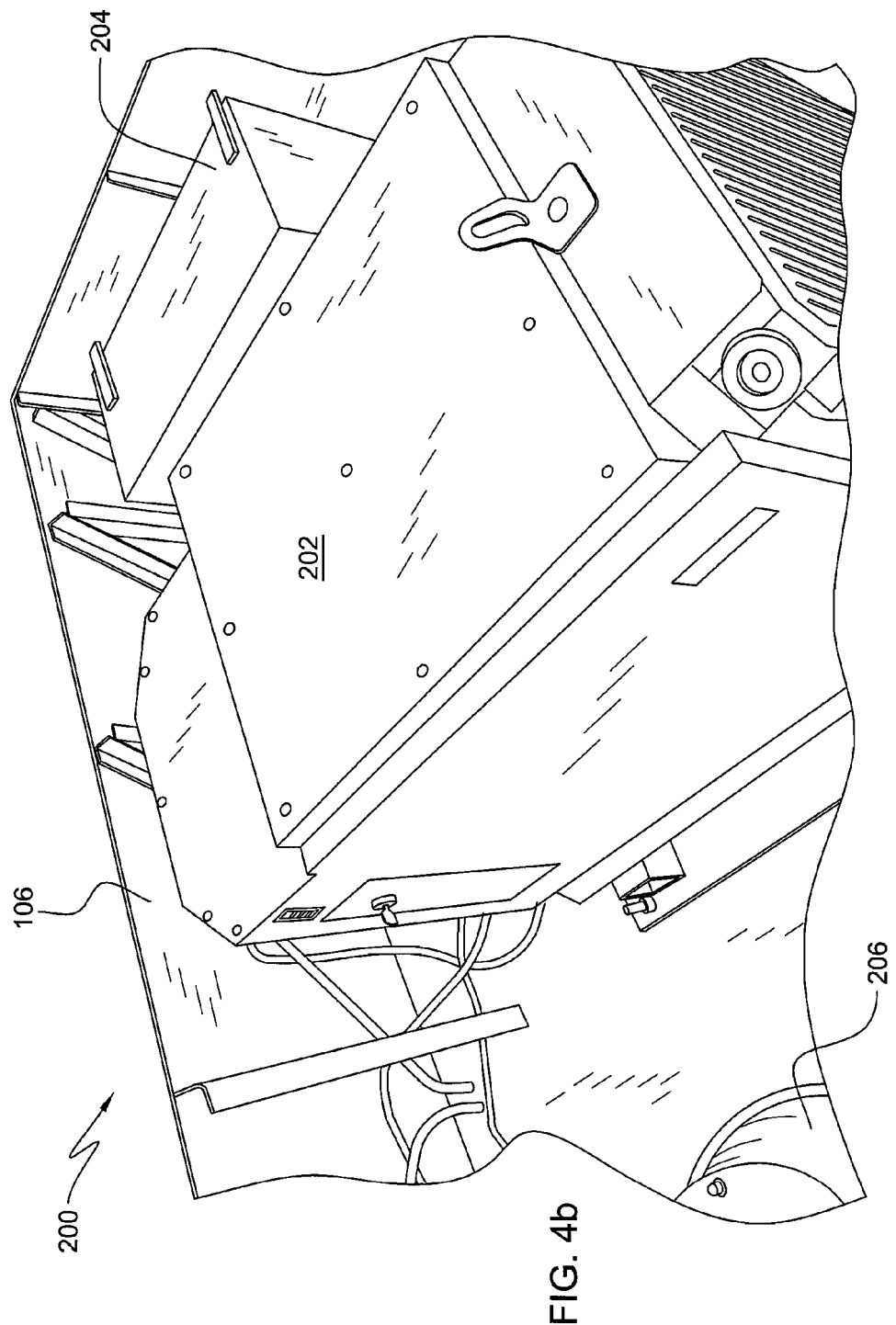

Referring now also to FIGS. 4a and 4b, there is shown a top plan schematic view and a pictorial, schematic view of the roof of vehicle 100, generally at reference number 200.

Three major components are mounted on roof 102 include: a generator 202, an air compressor 204, and a HEPA filter 208 that forms part of exhaust system 160.

Generator 202 is a three-phase, 208 volt, diesel powered generator capable of producing approximately 12 kW. Such capacity is required to power induction furnace 144 as well as all other electrical equipment associated with vehicle 100. While a Kubota Model 10012ENC, Engine type V1505BG has been chosen for purposes of disclosure, it will be recognized that other similar generators available from other manufacturers may be substituted. Consequently, the invention is not considered limited to a particular make or model of generator. Rather, the invention is intended to include any suitable generator. It should be noted that the vehicle may be powered from an external power source, typically with the exception of induction furnace 144. Induction furnace typically requires too much power to rely on any but an extremely high capacity external power source.

Air compressor 204 is a Porter Cable Model AC3P one horsepower compressor having a capacity of three gallons at 120 psi has been chosen for purposes of disclosure. Air supplied by air compressor 204 is used for driver, passenger, and rear air chairs 170, 172, and 124, respectively. In addition, compressed air supplied by air compressor 204 is available in assay facility 110 for utility purposes, primarily draining cooling water lines to induction furnace 144 to prevent cooling water from freezing within the furnace or cooling water lines, not specifically identified, during cold weather.

HEPA filter 208 removes most of the particles from the air being exhausted from inside truck 100, typically approximately 99.9% of particles greater than 0.3 microns.

Figure 5:
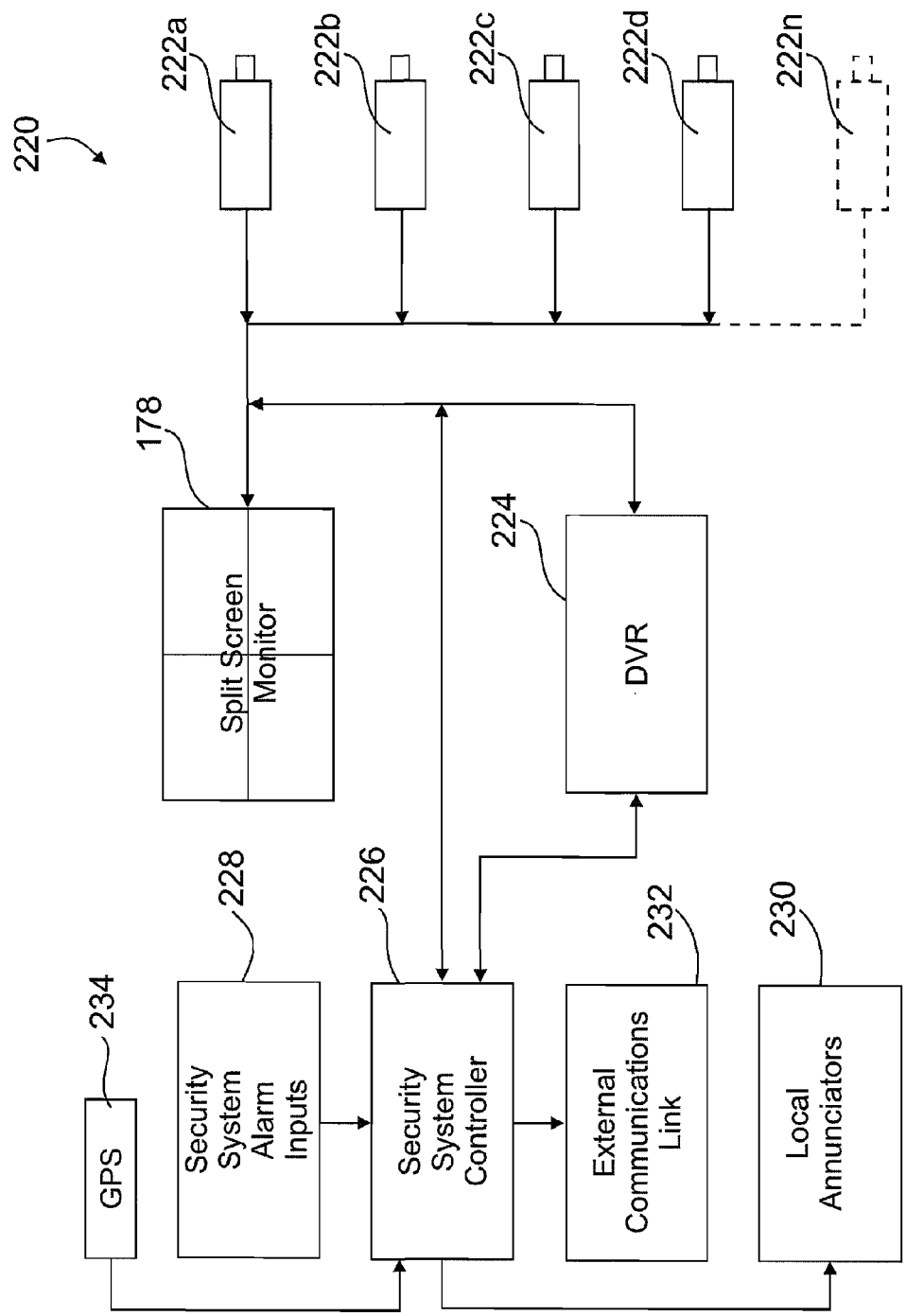
FIG. 5 is a simplified system block diagram of a security system forming part of the vehicle of FIGS. 1a and 1b.

Referring now to FIG. 5, there is shown a simplified system block diagram of a security system installed in vehicle 100, generally at reference number 220. Several security cameras 222a . . . 222n are deployed inside and outside vehicle 100 to provide visual monitoring of both the outside environment as well as interior activity in vehicle 100. At least four cameras 222a . . . 222n are typically installed. However, fewer or more cameras 222a . . . 222n may be used to address the requirements of a particular operating environment.

Cameras 222a . . . 222n are connected to monitor 178 within cab 112 of vehicle 100. Typically, monitor 178 is a split screen monitor and, in the embodiment chosen for purposes of disclosure, images from four different cameras 222a . . . 222n may be simultaneously displayed. It will be recognized that a video switcher, not shown, may be used to sequentially display the output of more than four cameras 222a . . . 222n. Such video switchers are believed to be well known to those of skill in the art and, consequently, are not further described or discussed herein.

Outputs from cameras 222a . . . 222n are also provided to a digital video recorder (DVR) 224 that continuously records images from all cameras 222a . . . 222n "whenever the vehicle is away from a base of operation.

DVR 224 is operatively connected to a security system controller 226 that is provided to manage all security/surveillance tasks in and around vehicle 100. The functions of DVR 224 are managed by security system controller 126.

A variety of security alarm inputs including but not limited to motion sensors, pressure sensors, vibration sensors, glass breakage sensors, safe intrusion sensors, sound sensors, fire sensors, power failure sensors, panic buttons, or any other known sensor or input, collectively referred to by reference number 228 are supplied as inputs to security system controller 226 for processing.

Also connected to security system controller 226 are local annunciators such as bells, sirens, lights, or other such devices, collectively referred to by reference number 230. Local annunciators 230 may be activated by security system controller 226 when a security system alarm input 228 causes security system controller 226 to deem that a security breach is suspected.

Security system controller 226 is also connected to an external communications controller 232 that typically maintains a constant connection to a base of operations, not shown. Communication is typically via a 3G/4G or similar cellular telephone network connection. However, the invention is not considered limited to a cellular telephone network connection. Rather, the invention is intended to cover any suitable wireless data communications link, known, or yet to be developed, over which digital data may be communicated. Typically, images from cameras 222a . . . 222n are transmitted to the base of operations (e.g., a central office or a branch office) via external communications link 232.

During a security alert situation, external communications controller 226 may also be adapted to contact local law enforcement officials using an automated 911 protocol. A GPS unit 234 connected to security system controller may be used to provide an exact location of vehicle 100.

During normal operations, GPS unit 234 provides the base of operations with a constantly updated location of vehicle 100.

In the embodiment chosen for disclosure, security system controller 226 forms part of dashboard/security system components 180 disposed in cab 112 of vehicle 100. Typically, all security is handled by a driver, not shown, who may remain secured in cab 112 as required while an assay technician, not shown, occupies and operated assay facility 110. As cab 112 and assay facility 110 are securely separated from one another, a security incident in assay facility 110 may be handled expeditiously by the driver in cab 112.

In operation, the mobile assay facility (i.e., vehicle 100) may be driven to a jewelry store, pawn shop, or other place of business having scrap gold for sale. For simplicity the term client will be used to represent any such facility or source of scrap gold or other precious metals.

Figure 6A:
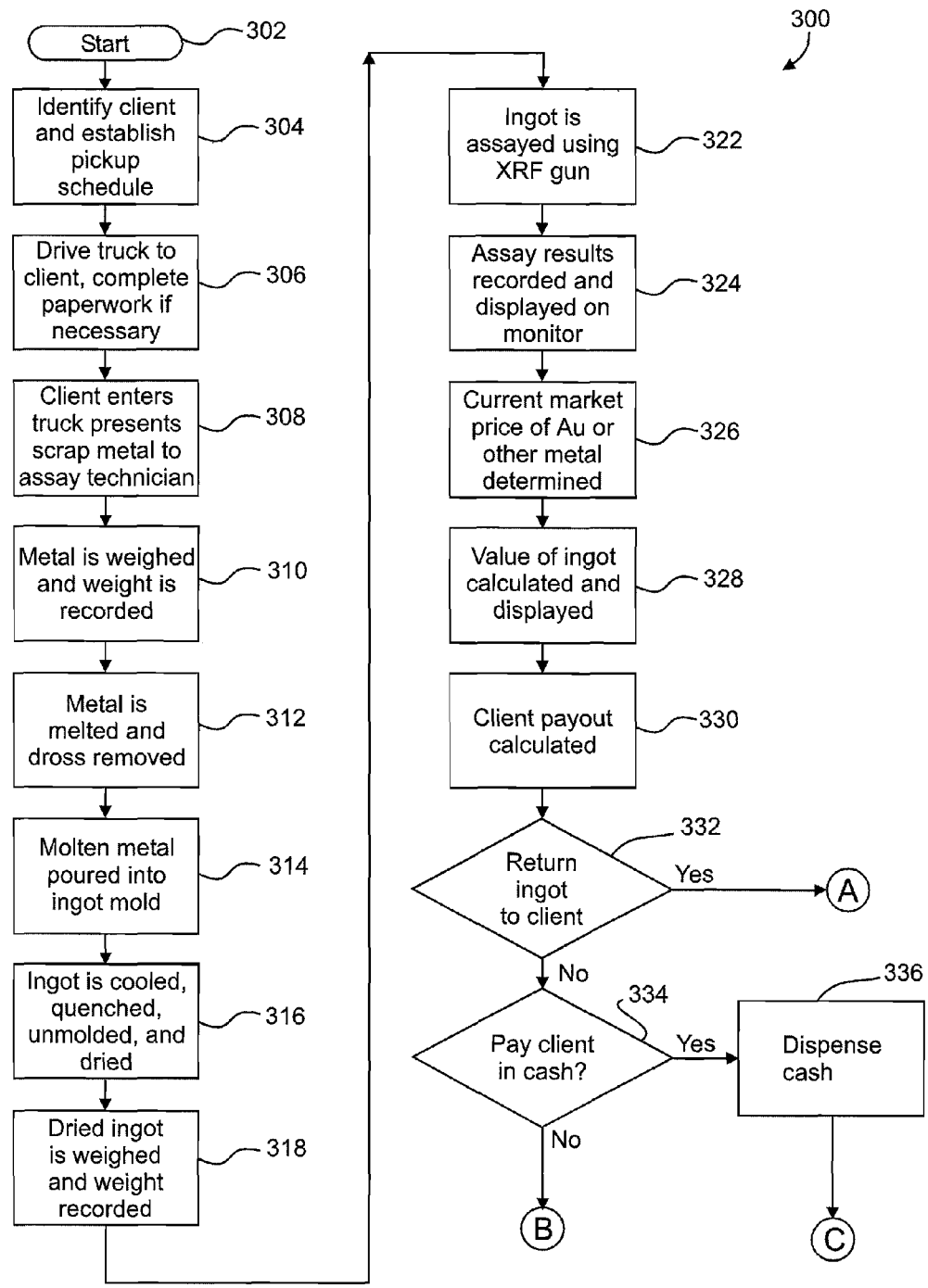
FIGS. 6a and 6b collectively form a flow chart showing a method of using the mobile assay facility of the invention.
Figure 6B:
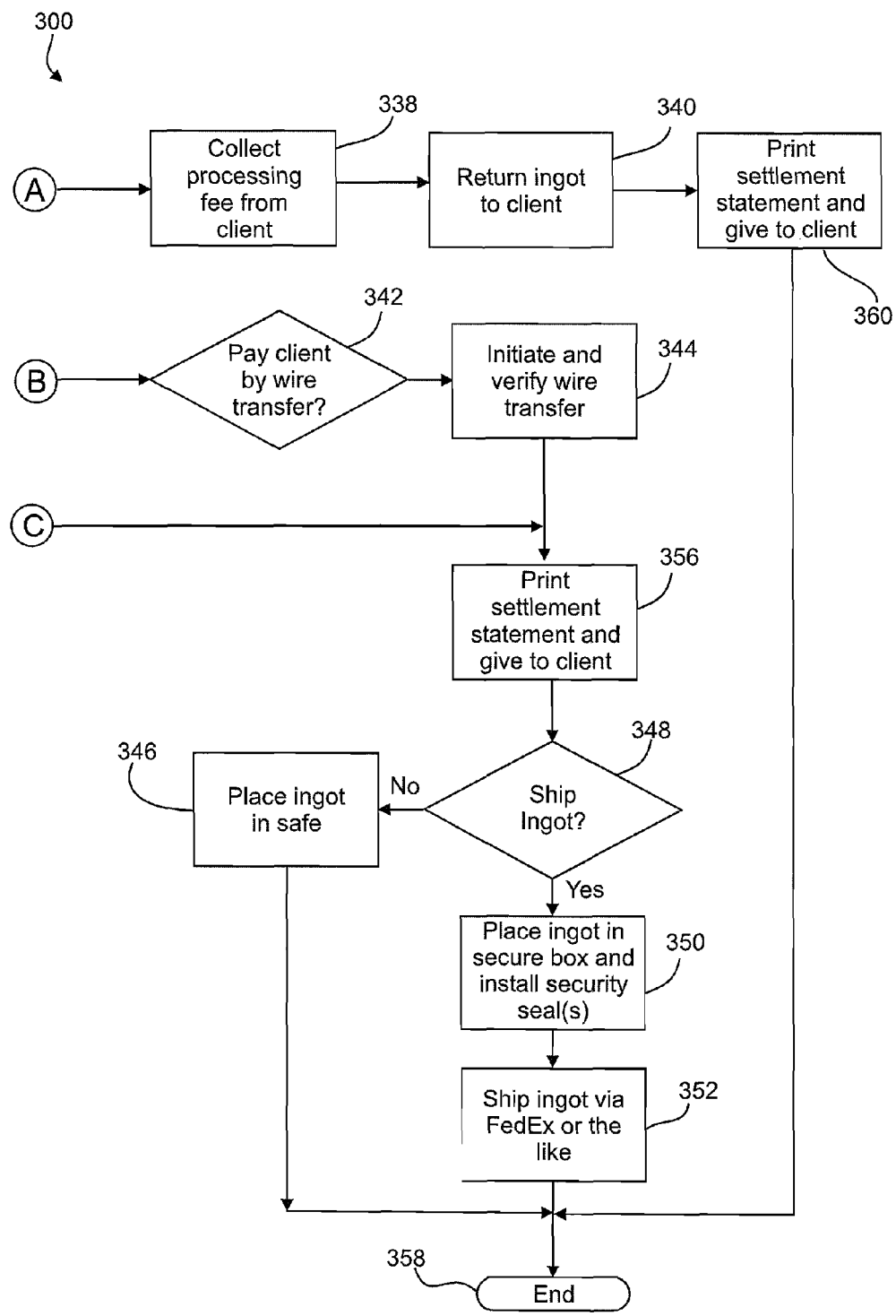

Referring now to FIGS. 6a and 6b there is collectively shown a flow chart of the mobile assay process of the invention, generally at reference number 300.

The process is started, block 302. Once a client is identified, and a pickup schedule established, block 304 vehicle 100 is driven to the client's site. When required any necessary paper work for compliance with 13 C.F.R. §103.140 or other anti money laundering statutes must be completed, block 306.

The client is invited into assay space 110 and the client presents scrap jewelry or other scrap gold or other precious metals to the assay technician, block 308. Typically an inconspicuous collection container, not shown, is provided to each client so that the movement of the container is unlikely to arouse suspicion in anyone observing the physical transfer of the scrap gold between the client's facility and vehicle 100. In one embodiment, a two-gallon paint pail is used. It will be recognized that many alternate containers may be substituted therefor.

The bucket and its contents are first weighed using analytical balance 132, block 310. Scrap gold is then transferred into a crucible, not specifically identified, that is placed in crucible opening 146 of induction furnace 144. Typically, induction furnace has been started and has been allowed to reach a desired melting temperature, generally approximately 2000° F. Scrap gold is generally added in small amounts. The melted precious metal mix is periodically stirred to obtain a uniform mixture of the component metals of the batch. Unmelted metals such as Platinum (Pt) are removed from the melt as is dross, block 312.

When the melt is at an appropriate temperature, considered to be uniform, and is free from dross, the crucible is removed from induction furnace 144 and the contents poured into an ingot mold of an appropriate size, block 314.

Once the poured ingot has cooled sufficiently for safe handling, the ingot is removed from the ingot mold and placed into quench tank 134 for rapid cooling.

When cool, the ingot is removed from quench tank 132. The ingot is then dried, block 316. Once dried, the ingot is weighed on analytical balance 132 and the weight recorded, typically in computer 174 within cab 112, block 318. Analytical balance 134 has an interface, not shown, that allows its electrical connection to computer 174.

Figure 7:
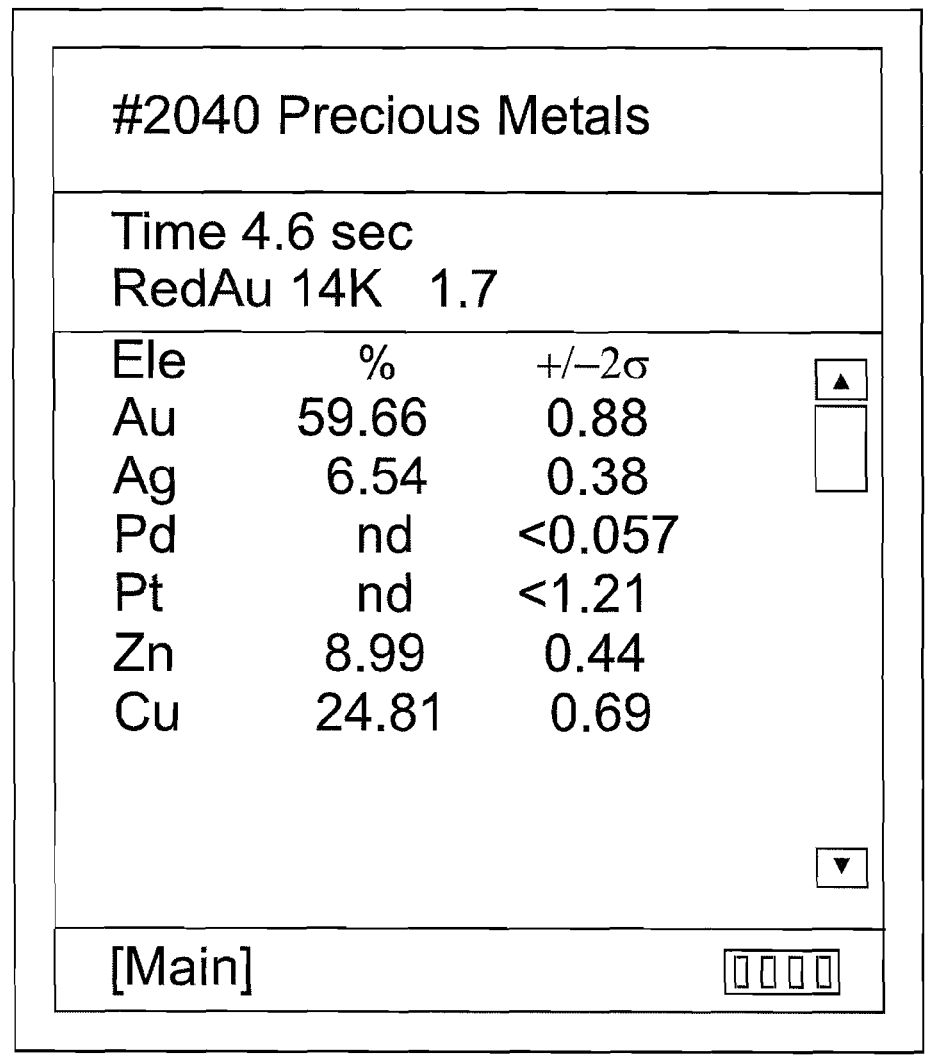
FIG. 7 is a screen shot of an assay of an ingot formed as part of the method of FIGS. 6a and 6b.

After weighing, the ingot is scanned by XRF analyzer 130, block 322 and the results of the X-ray analysis recorded and displayed, block 324. A screen shot of a typical analysis result is shown in FIG. 7. As may readily be seen, the percentage and a two sigma value for various component metals of the ingot are displayed. In the example shown in FIG. 7, gold (Au) forms 59.66 with a 2σ value of 0.88. Likewise, the percentage of Silver (Ag), Palladium (Pd), Platinum (Pt), Zinc (Zn) and copper (Cu) are displayed.

The market value of the selected precious metal (e.g., gold) in the ingot is calculated, block 326 and is determined by first obtaining the current market value of gold, block 326. The value of the selected precious metal (e.g., gold) is calculated by multiplying the current market value by the percentage of the metal in the ingot multiplied by the total weight of the ingot. Weights are typically expressed in ounces although it will be recognized that other units of measure, for example, grams may be used for such calculations.

Figure 8:
FIG. 8 is a settlement form displaying information regarding the value and fees associated with precious metal being procured from a seller thereof in accordance with the method of FIGS. 6a and 6b.

Once the market value of the precious metal is known, a client payout for the ingot may be calculated. Referring now also to FIG. 8, there is shown a form that may be used to determine the payout to the customer, generally at reference number 380.

For simplicity, for purposes of illustration gold will be used. It will be recognized, however, that any precious metal of interest may be substituted for gold used for purposes of disclosure. The percent (%) purity value resulting from the X-ray analysis, block 324 is transferred to form 380 and shown at reference number 382.

The total ounces of gold 384 are calculated by converting (when necessary) the bar or ingot weight in grams to ounces and multiplying by the % pure, 382.

The market price of gold obtained at block 326 is also transferred to form 380 and placed on the form at reference number 386.

A total amount 388 is obtained by multiplying the total ounces of gold 384 by the current market price 386.

A processing fee of 5% is applied to the transaction. The processing fee is subtracted from the total amount 388 to net proceeds (minus charges) that are to be paid to the client, reference number 390. While a 5% processing fee has been chosen for purposes of disclosure, it will be recognized that other processing fee percentages, fixed, or sliding scale, may be substituted for the 5 percent value chosen for purposes of disclosure.

Three additional fees, a processing fee 392, a shipping fee 394, and a wire transfer fee 396 may optionally be subtracted from the 95% of total value 390 to calculate the net customer payout 398 due to the client.

A processing or handling fee 392 may be applied to small orders to help cover the overhead of driving vehicle 100 to a client for a small batch.

Shipping fee 394 may be imposed if a melted ingot is to be shipped to a buyer.

Wire Fee 396 may be charged to cover the expense of paying a client via a wire transfer.

Once any fees 392, 394, 396 are subtracted, a net customer payout 398 is calculated, block 330.

There are several ways in which the customer may be paid for the scrap metal. One way is to simply return the ingot to the customer and charge the customer a processing fee for the assays, block 332. Once the processing fee is collected, either in cash or by another arrangement, block 338, the ingot is returned, block 340, a client statement is printed, block 360 and the process is terminated, block 358.

If the client chooses to be paid in cash, block 334, the appropriate amount is dispensed, block 336 by cash dispenser 154 controlled by the driver within cab 112. A client statement is then printed, block 356, and control is passed to block 348.

If, however, the client chooses to be paid by wire transfer to his or her account, block 342, a wire transfer is executed, block 344 by the driver within cab 112. Typically, a client does not leave assay facility 110 until a verification of the wire transfer, including a confirmation number, is received and passed on to the client. A client statement is printed, block 356 and control is passed to block 348.

If the client has surrendered the ingot, it will either be shipped or put into safe 140. If the ingot is to be shipped block 348, it may be put into a so-called turtle box and sealed with one or more security seals, block 350. The turtle box is then placed into a suitable shipping box and shipped, block 352. For purposes of disclosure FedEx® will be used as the shipping service. It will be recognized that other suitable shippers may be substituted for FedEx. Typically overnight service is used to ship an ingot to a buyer.

If the ingot is not to be shipped, block 348, it is placed into safe 140, block 346.

Because vehicle 100 is equipped with complete communications facilities including Internet access, the ingot buyer may be alerted to expect an ingot and given the shipping bill number and the assay analysis of the ingot. By suitable arrangement with the ingot buyer, payment for the ingot may be made to the seller via a wire transfer thereby minimizing float.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:
1. A mobile assay facility, comprising:
a) a mobile vehicle suitable for containing all tools and equipment required to melt and assay precious metals, said vehicle being adapted to allow a seller of precious metals to observe the melting and assaying processes;

b) a scale disposed within said vehicle and positioned within view of said seller, said scale being adapted to output a signal representative of a weight of an object weighed thereupon;

c) a furnace disposed in said vehicle adapted to melt precious metal received from said seller, said furnace disposed within view of said seller and adapted to melt said precious metal to produce an ingot;

d) an X-ray fluorescence (XRF) alloy analyzer disposed in said vehicle within view of said seller and adapted to analyze said melted ingot and to record and display the results of an analysis thereof;

e) means for determining a current market price of a particular precious metal of interest present in said ingot disposed proximate said vehicle;

f) a computer adapted to receive at least said signal representative of a weight of an object weighed received from said scale, an output recorded by said XRF analyzer, said determined current market price of said particular precious metal of interest and adapted to perform at least a calculation of the market value of said precious metal component of said ingot; and g) a printer adapted to print at least the result of said calculation.

2. The mobile assay facility as recited in claim 1, wherein said mobile vehicle comprises a vehicle comprising a cab portion and a cargo portion.

3. The mobile assay facility as recited in claim 2, wherein said truck comprises a modified armored truck comprising a cab portion and a cargo portion separated therefrom by a secure partition, a roof in at least said cargo portion being raised a predetermined amount to provide standing room in said cargo portion for an upright adult human.

4. The mobile assay facility as recited in claim 3, wherein said predetermined amount is approximately 18 inches.

5. The mobile assay facility as recited in claim 3, wherein said modified armored truck comprises indicia on an exterior thereof.

6. The mobile assay facility as recited in claim 5, wherein said indicia comprises at least one from the group: advertising, and misleading indicia to disguise the function of said vehicle as a mobile assay facility.

7. The mobile assay facility as recited in claim 3, further comprising:
h) a computer display disposed in said cargo portion of said vehicle and operatively connected to said computer; and
i) a seat disposed in said cargo region and positioned to provide an occupant thereof a view of at least said scale, said XRF analyzer, said induction furnace, and said computer display.

8. The mobile assay facility as recited in claim 2, wherein said furnace comprises:
i) an induction furnace;
ii) a source of cooling water therefor operatively connected thereto; and
iii) an exhaust hood disposed adjacent said induction furnace and adapted to remove fumes generated by said induction furnace from within said cargo portion.

9. The mobile assay facility as recited in claim 8, wherein said source of cooling water comprises a two stage cooling apparatus comprising: a water storage tank, and a chiller apparatus operatively connected thereto, said two stage cooling apparatus being operatively connected to said induction furnace.

10. The mobile assay facility as recited in claim 2, further comprising:
h) an ingot cooling tank disposed proximate said induction furnace within said cargo portion of said vehicle.

11. The mobile assay facility as recited in claim 2, further comprising:
h) a safe disposed within said vehicle and adapted to receive at least said ingot.

12. The mobile assay facility as recited in claim 2, wherein said computer is of a type selected from the group: laptop computer, notebook computer, netbook computer, tablet computer, and other portable computer system.

13. The mobile assay facility as recited in claim 2, further comprising:
h) an electrical generator configured to supply electrical power to at least said furnace.

14. The mobile assay facility as recited in claim 13, wherein said electrical generator comprises a three-phase, diesel powered electrical generator.

15. The mobile assay facility as recited in claim 13, wherein said generator is mounted on a roof of a cargo region of said vehicle.

16. The mobile assay facility as recited in claim 2, further comprising:
h) a security and surveillance system disposed in and around said vehicle, said security and surveillance system comprising:
i) at least one camera disposed at a location selected from the group: inside said cargo portion, inside said cab portion, and outside said vehicle;
ii) a monitor disposed inside said vehicle operatively connected to display an image from said at least one camera;
iii) a digital video recorder operatively connected to and adapted to record an image from said at least one camera;
iv) a communications link operatively connected to at least one of said at least one camera and said digital video camera operatively connected to each thereof and adapted to transmit at least an image therefrom to a receiver at a location remote from said truck.

17. The mobile assay facility as recited in claim 16, wherein said security and surveillance system further comprises:
v) at least one alarm input selected from the group: motion sensors, pressure sensors, vibration sensors, glass breakage sensors, safe intrusion sensors, sound sensors, fire sensors, power failure sensors, panic buttons, other alarm sensors; and
vi) at least one local annunciator selected from the group: bells, sirens, lights, or annunciators devices.

18. The mobile assay facility as recited in claim 2, further comprising:
h) an air compressor disposed on a roof of said vehicle.

19. The mobile assay facility as recited in claim 2, further comprising:
h) communications system disposed in said vehicle for establishing and maintaining at least digital communication with a location remote from said vehicle and for providing Internet access to said mobile assay facility.

20. The mobile assay facility as recited in claim 2, further comprising:
h) an air conditioner disposed in said cargo portion of said vehicle.

* * * * *

UNITED STATES PATENT AND TRADEMARK OFFICE
CERTIFICATE OF CORRECTION

PATENT NO.        : 8,551,402 B1
APPLICATION NO.   : 13/364422
DATED             : October 8, 2013
INVENTOR(S)       : Noyes It is certified that error appears in the above-identified patent and that said Letters Patent is hereby corrected as shown below:

Title Page item (63) change:
"Continuation-in-part of application no. 13/136,811, filed on Aug. 11, 2011." to:
-- Continuation-in-part of application no. 13/136,811, filed on Aug. 11, 2011; and Application No. 13/364,422, filed February 2, 2012 is a Continuation-in-Part of Application No. PCT/US2011/066807, filed December 22, 2011, which is a Continuation-in-Part of Application No. 13/136,811, filed August 11, 2011. --

In the Specification

Column 1 lines 5-11 change "Related Applications:

This application is a Continuation-in-Part application of U.S. Patent Application No. 13/136,811 filed August 11, 2011 titled Mobile Assay Facility and Method of Using Same to Procure and Assay Precious Metals which is included herein in its entirety by reference." to:
-- CROSS REFERENCE TO RELATED APPLICATIONS This Application No. 13/364,422, filed February 2, 2012 is a Continuation-in-Part of Application No. 13/136,811 filed August 11, 2011, which is incorporated by reference herein in its entirety; and
Application No. 13/364,422, filed February 2, 2012 is a Continuation-in-Part of Application No. PCT/US2011/066807, filed December 22, 2011, which is a Continuation-in-Part of Application No. 13/136,811, filed August 11, 2011. --

Signed and Sealed this
Twenty-seventh Day of May, 2014

Michelle K. Lee
*Deputy Director of the United States Patent and Trademark Office*